US011096819B2

(12) United States Patent
Brown

(10) Patent No.: US 11,096,819 B2
(45) Date of Patent: Aug. 24, 2021

(54) MENSTRUAL DEVICE WITH PRESSURE POINTS AND ELONGATED REMOVAL STEM

(71) Applicant: Christine Beatrice Brown, Carpinteria, CA (US)

(72) Inventor: Christine Beatrice Brown, Carpinteria, CA (US)

(\*) Notice: Subject to any disclaimer, the term of this patent is extended or adjusted under 35 U.S.C. 154(b) by 68 days.

(21) Appl. No.: 16/237,172

(22) Filed: Dec. 31, 2018

(65) Prior Publication Data
US 2020/0206019 A1 Jul. 2, 2020

(51) Int. Cl.
*A61F 5/00* (2006.01)
*A61F 5/455* (2006.01)

(52) U.S. Cl.
CPC ................... *A61F 5/4553* (2013.01)

(58) Field of Classification Search
CPC ...... A61F 5/4553; A61F 13/2045; A61F 6/08; A61F 13/5519; A61F 13/55145; A61F 13/55105; A61F 13/55175
See application file for complete search history.

(56) References Cited

U.S. PATENT DOCUMENTS

| 1,891,761 | A | * | 12/1932 | Goodard | ............... | A61F 5/4553 |
| | | | | | | 604/330 |
| 4,381,771 | A | * | 5/1983 | Gabbay | .................... | A61F 6/08 |
| | | | | | | 128/836 |
| 10,617,556 | B2 | * | 4/2020 | Russe | .................... | A61H 19/40 |
| 10,806,624 | B2 | * | 10/2020 | Brockway | ............ | A61F 5/4553 |
| 2018/0214298 | A1 | * | 8/2018 | Medas | ................. | A61F 5/4553 |
| 2019/0224039 | A1 | * | 7/2019 | Garriga I Rodo | .... | A61F 5/4553 |
| 2019/0336318 | A1 | * | 11/2019 | Kubo | .................... | A61F 5/4553 |
| 2019/0388264 | A1 | * | 12/2019 | Russe | .................... | A61H 19/40 |
| 2020/0214876 | A1 | * | 7/2020 | Tsai | ....................... | A61F 5/4553 |

\* cited by examiner

*Primary Examiner* — Steven O Douglas

(57) ABSTRACT

An asymmetrical menstrual device with functional pressure points that aid in the insertion, opening, and removal of the device and requires minimal contact with the device itself, as well as with the body while placing inside the vaginal canal. Major design elements support ease of placement and effective opening of the device to create a seal, while minimizing pressure in sensitive areas. Another design feature is the length, functionality, and malleability of the removal stem that can be adapted to any length up until the base of the device. These elements enable greater cleanliness, comfort, and overall ease of use.

20 Claims, 14 Drawing Sheets

MENSTRUAL DEVICE WITH PRESSURE POINTS AND ELONGATED REMOVAL STEM

FIELD

A menstrual device with pressure points, asymmetrical shape, elongated removal stem, and various elements that provide more comfort and ease during insertion, during wear and usage, and removal. A major part of the device is the method to apply pressure and fold the device with one hand, thereby allowing minimal contact to the device.

BACKGROUND

Menstrual cups (also sometimes referred to as "devices") are products that are placed within the vaginal canal and allow the user to collect menstrual fluid. The materials used can vary, but should include medical grade silicone for safety and hygienic purposes. Cups can be reused for several years, pending proper care, thus reducing the overall cost and amount of waste other menstrual products, such as pads and tampons, create. Cup options have been on the rise in the marketplace, but there has been a need for designs that address discomfort, sometimes even pain, that is associated with insertion, removal, as well as difficulty creating a proper seal that diminishes the likelihood of leakage. Cups often require two hands to properly fold or pinch down the material and then put in place, and often require additional skin contact with the labia, as well as within the vaginal canal, to ensure it is properly placed with the seal of the upper ring intact. This can be problematic as placing or removing a cup can be messy and access to running water or other means to clean the cup prior to re-insertion and wash one's hands can sometimes be limited.

SUMMARY

By designing a menstrual device that is asymmetrical, it enables greater comfort and functionality during insertion and removal and reduces the possibility of leakage due to the unique integrity of the device shape that lends itself to fully opening once placed in the vaginal canal.

The disclosed design features provide a menstrual device in which comfort, functionality, and methods for insertion and removal are major elements of the overall asymmetrical shape.

The base of the device extends into an elongated stem that can be adapted by the user to their desired length to any length up until the base of the device. The elongated stem also minimizes the need for additional skin contact or possible probing inside the vaginal canal to establish the device location.

The base of the device exhibits areas with functional pressure points for collapsing the device with one hand instead of two; ensuring a full pop-open or seal of the upper ring when placed in the vaginal canal; and enabling a gentle breaking of the seal for comfort and ease of removal.

Further features, advantages and properties of the device associated with this application; will become clear in the detailed descriptions.

BRIEF DESCRIPTION OF THE DRAWINGS

In the following detailed section of the present description, the elements of the present application will be explained in greater detail with reference to the example embodiments included in the drawings, in which.

DETAILED DESCRIPTION

Figure 1:
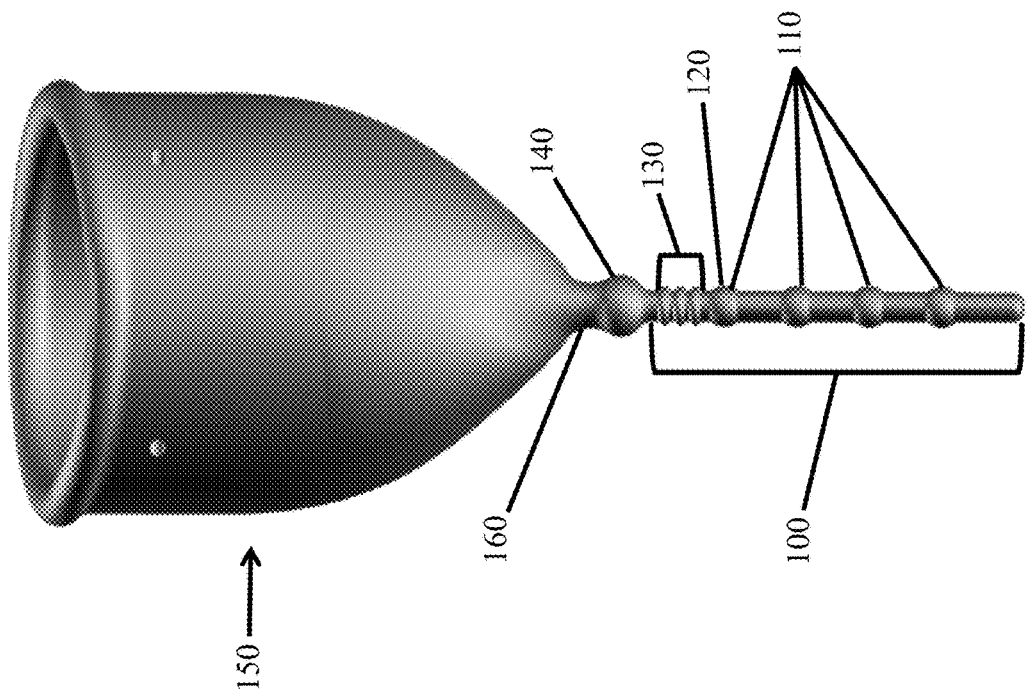
FIG. 1 is a perspective view of a menstrual device from the front with an elongated removal stem in accordance with aspects of the present invention.

The vaginal cavity is quite adaptable and varies slightly with each individual. It is where menstrual blood exits from the cervix in various amounts for a duration, typically, of several days each month. Methods and products for menses range from absorption, with pads and tampons, to collection, with catamenial devices, now more commonly known as menstrual cups.

Menstrual cups provide a healthy and sustainable alternative to the waste accumulating one-time usage of pads and tampons. Menstrual cups can be made from silicone via a liquid silicone rubber, silicone injection molding process, and with proper care can be used for several years. However, it is challenging to find a product that has gone through the full certification and validation processes. This can impact the overall quality in available products, ranging from the materials used, to their manufacturing and post-manufacturing processes, resulting in products that may be suspect.

Menstrual cups, with increasing popularity and awareness, has become a more common menstrual solution—especially amongst those who wish to reduce waste and save money with a healthy alternative, but many are hindered by the needed body contact to place and remove the cup and fear it will be messy. To properly place a traditional menstrual cup, the user will need to pinch or press down the sides of the cup wall to collapse it and make it smaller for insertion. This, traditionally; has required contact on all outer wall surfaces of the cup and the use of two hands. Similar to a tampon, the cup is then inserted into the vaginal canal, where it will need to open, or unfold, in order to ensure a seal. The goal of the seal, which is achieved by continuous contact on the sides of the vaginal wall by the upper ring of a cup, is to prevent the possibility of leakage. Most cups will require the user to have additional physical contact of their labia as well as inside their vaginal walls to check and make sure a cup is properly placed and fully open, thereby creating the desired seal for collection. This process sometimes involves: manual examination within the vaginal cavity with a finger along all sides of the wall to check for a folded area or crease; additional cup rotation within the vaginal canal with hopes that it will eventually open fully; or other similar actions, which is more involved than many might be comfortable with, and can be messy. There is not always access to clean, running water, so this part of the process might prove problematic for some, increasing the risk of being unhygienic in those instances. Further, checking to make sure a cup is properly placed each time might take more time than some prefer. However, cups generally have a larger capacity than tampons or pads, so some users are able to go up to twelve hours between emptying their cup, thus plan accordingly and wait until they are in a more favorable location to wash their hands and empty the cup, also saving time overall due to less frequent changing demands compared to tampons or pads.

Some cups tty to avoid this additional contact inside the vaginal canal to check or manually create a seal, by designing a thick or stiff upper ring that has a stronger pop-open, but this, in turn, might be painful or uncomfortable for some users. Further, having increased pressure at the top of the cup, that is the furthest distance into the vaginal cavity, can create an undesired effect of additional pressure on the urethra and colon, creating a sensation of needing to urinate, or restricting that process. It can also create a sensation of blockage or constipation in the user when it comes to bowel movements. The female anatomy of the urethra and colon are closer in proximity to the vaginal cavity the further into the vaginal canal one goes. Conversely, there is less impact on other bodily functions or discomfort if there is rigidity or pressure closer to the vaginal opening where the spacing of the urethra and colon are further from the vaginal canal. Furthermore, when it's time to remove and empty the cup, the thick or stiff upper ring that is no longer collapsed like it was during insertion, but fully open, can cause pain for some users in that it's a much larger area that's being removed from the vaginal canal.

Most cups, while they are malleable, are symmetrical in shape, which does not take into account the overall shape of the vaginal cavity. This can create slight discomfort and awareness when a symmetrical cup is being used. Sometimes those cups go beyond discomfort and cause irritation, rubbing or rashes, soreness, bruising of the cervix, near the public bone, or other areas in or near the vaginal canal, in part, due to their symmetrical shape. It should also be noted that small holes can be seen near the upper ring of most cups, which help to maintain a balance in bodily fluids and relate to the effectiveness of the seal.

Removal of the cup to empty, clean, and reinsert if still menstruating, can require intimate contact as opposed to a pad or tampon, which can be removed with an attached string. Most cups have a base with little or no material to grasp and pull the cup down and out of the vaginal cavity. Some have a base or stem that extends to almost an inch in length and are not necessary for the overall function of the cup and can be cut or removed completely if the user desires due to having a lower cervix, or if they have sensitivity to the often abrasive material extending out from the stem to create a grip. The abrasive materials can cause friction, create discomfort, and sometimes even a rash, especially when extending from a cup base or stem that is quite substantial in material width. The stem in some cups may be covered with small "spikes" or the like, insofar that it might feel to a user like a stiff popsicle stick or straw with extending ladder rungs, or like rough sandpaper against delicate tissues. In cups with minimal or no stem at the base, the user might need to search for the cup by reaching up and into the vaginal cavity because the cup might have shifted higher or out of place during use—especially in the case of individuals who have a higher cervix. This can prove problematic, again, in cases where one can't properly clean their hands before or after, or in situations where someone might have longer fingernails, as they might inadvertently scratch themselves, or damage the cup as they try to grab hold of the cup and pull it out for removal.

Once the user has hold of the cup, due to the often stiff upper ring that is now fully open, resulting in a much larger surface area and circumference than the previously, collapsed cup for insertion, removal can sometimes create discomfort or even pain for the user. This, along with some of the many other aspects found in traditional cups described above, can deter someone from continuing usage of a cup.

Therefore, it is the aim of this present design to address prevalent limitations and provide a more comfortable, functional, and reliable menstrual device. Such design, while being more user friendly for first-time and long-time cup users, may also benefit individuals with disabilities due to a more functional and user-friendly insertion and removal process. Additionally, considering social and cultural stigmas and taboos often still surrounding menstruation, female bodies, and physical contact, this particular design may help alleviate stigmas insofar as the device requires far less physical contact for placement and removal compared to traditional cups. Further, it is of utmost importance that the material sourced and used for manufacturing has gone through extensive biological testing in order to obtain regulatory clearance for medical device usage. Manufacturing aims to meet all federal requirements and is certified, registered, and listed to produce such medical devices, which is in opposition to current market trends where products don't always follow such procedures.

The material of the menstrual device may be made from medical grade silicone. The medical grade silicone may be designed to meet Current Good Manufacturing Practice, (cGMP) standards in facilities directly or indirectly regulated by US FDA (Food and Drug Administration). The liquid silicone rubber, or LSR, is designed for liquid injection molding, or LIM, as well as overmolding, which is another production option. The present design may also minimize production waste during the LIM process since the removal stem may also function as the channel in which the LSR travels within the tool or mold when manufacturing the menstrual device. In some devices, the material range can be 40 to 70 durometers, depending on specific design, function, and desired product feel. It should be noted that the device can be made with or without a removal stem, with or without additional grips on the stem or base or the cup, from alternate materials, with alternate manufacturing processes.

It is noted that this list is not exhaustive as there may be other advantages not explicitly detailed herein. Further, the present application includes features and descriptions that can be implemented in combinations other than those explicitly, described.

A first perspective of the menstrual device is illustrated in FIG. 1. The device 150 has a noticeably long and slender removal stem 100. Removal of the device 150 with the stem 100 should enable less probing if a user has a high cervix, or the device moves further up in the vaginal canal during wear, thus creating a safer and cleaner removal process. The existence of a removal stem is not unique per se, but this particular removal stem 100 is useful because it is noticeably elongated, yet remains highly flexible for increased comfort due to the stem width that does not need to be uniform in width, and can range from 1.5 mm to 6 mm. Removal stem 100 can be adapted to any length up until the removal bulb 140 or base of the device 160, by cutting the stem 100 to the desired length of the user. In some devices, the removal stem 100 may comprise small bulbs 120 that may vary in width and function both as a grip during removal or as a unique reference 110 for if a user wanted to shorten the stem. The user may do so by counting the number of bulbs 120 from the tip of the stem 100, removing the cup 150 from their body, then using that reference number to cut the stem 100, thereby eliminating what stem 100 length might not be needed for their body. The stem 100 can range in length from 0 mm, if removed, to just under 50 mm. Further comprising, the stem 100 is singly molded with the base of the device in uniform material, which due to the unique length and dimensions, is useful because it creates a reusable removal stem. Alternatively, users might otherwise have to add a one-time-use string, other material, or approach that might prove less healthy or sustainable in order to create additional length for ease of access.

A second perspective view in FIG. 1, the stem 100 may thrther comprise of one or more removal grip rings 130 in the removal stem 100, providing traction while also minimizing potential for friction or discomfort from rough or protruding edges. The existence of additional material or grips 130 is not unique per se, but this particular placement of the grips 130 and unique contoured shape of the grips 130 and bulbs 120 assists in removal, while limiting potential for irritation. Alternatively, the device 150 is manufactured without the existence of the grips 130, removal stem 100, and/or the removal bulb 140 at the base 160.

Figure 2:
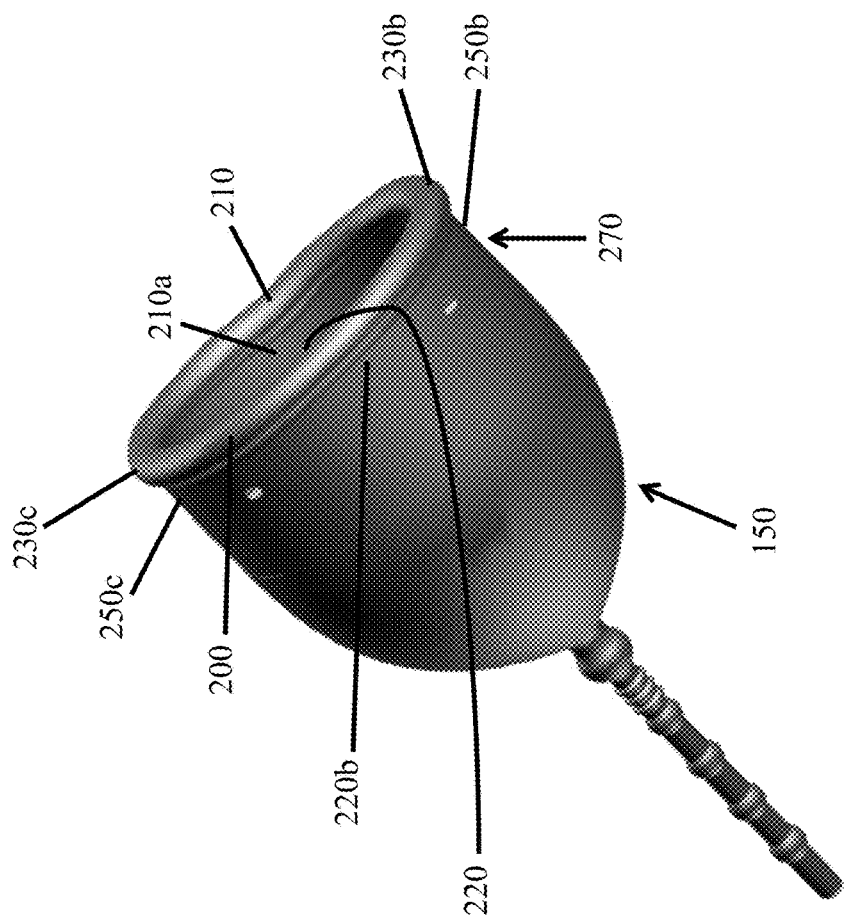
FIG. 2 is a perspective view from the back; with a slightly elevated angle, of the menstrual device of the present invention.
Figure 13:
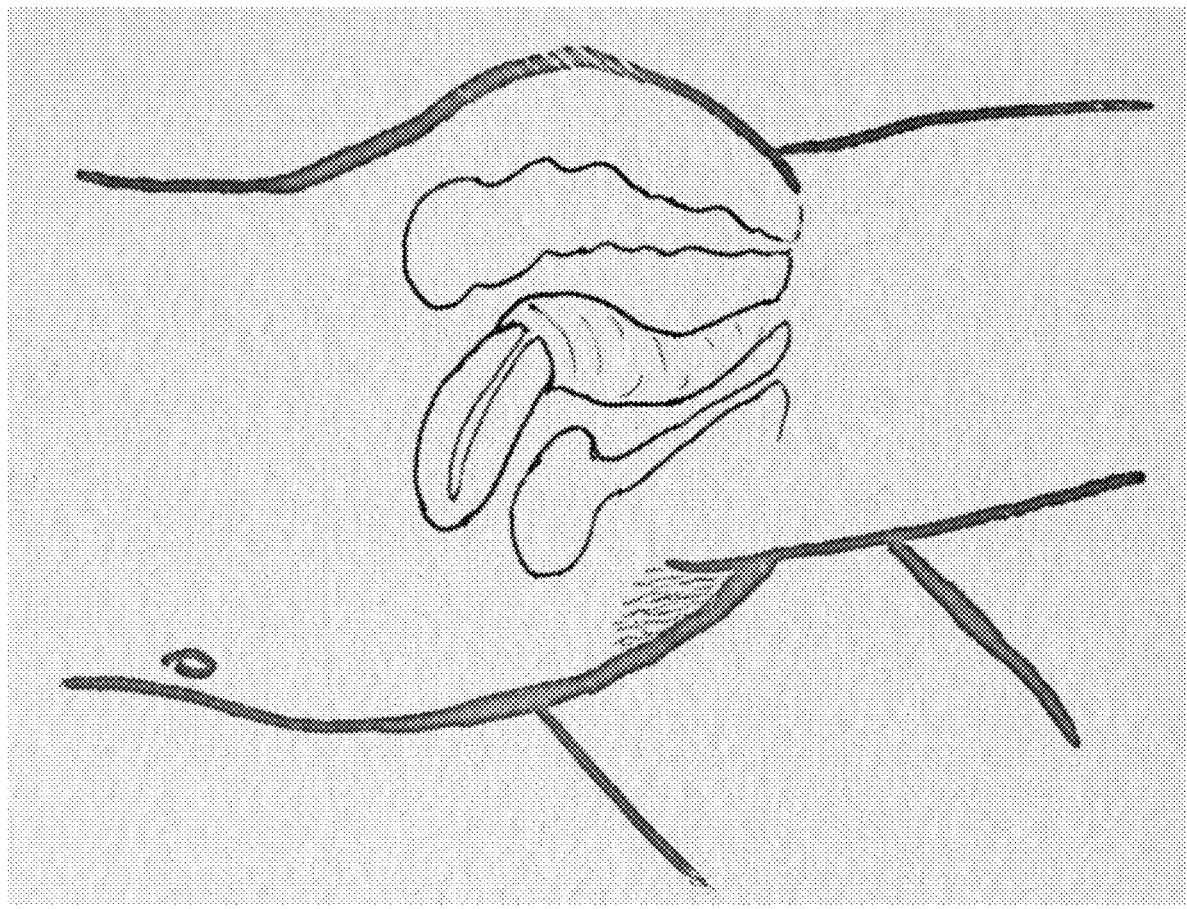
FIG. 13 is a side cutaway view of the female anatomy showing the urethra, vaginal canal, and colon.
Figure 14:
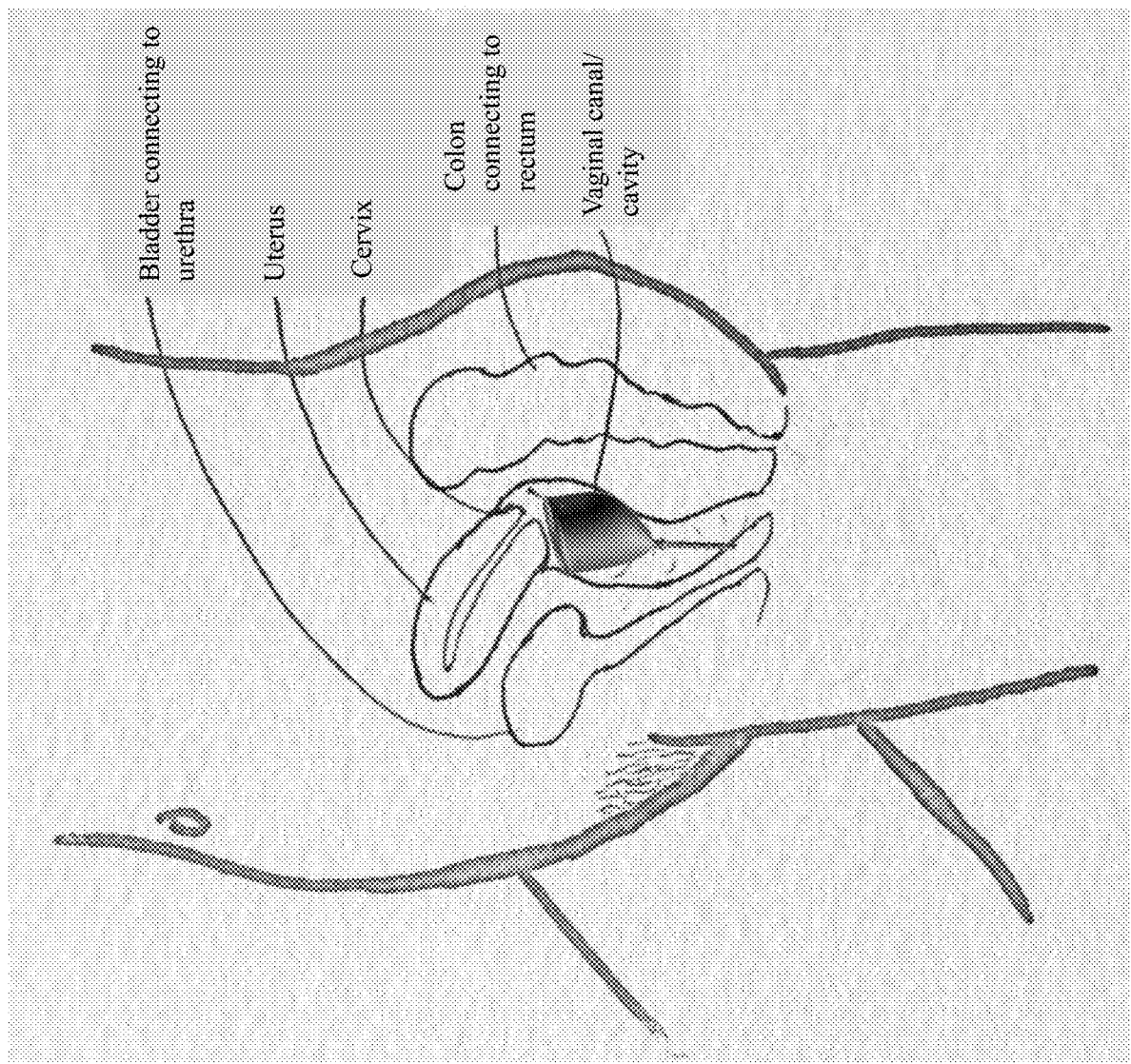
FIG. 14 is a side cutaway view of the female anatomy with a menstrual device placed inside the vaginal canal.

In the exemplary perspective view of FIG. 2, an upper ring 200 is viewed from the back, and slightly above, the cup 150. The existence of the upper ring 200 is not unique per se, but it should be noted that the upper ring 200 is not uniformly within the inner diameter of a cup wall 270, nor is it uniformly extending out as an outer diameter ring from the cup wall 270. It should be noted that this particular upper ring 200 is useful because it provides needed continued contact against the vaginal wall while minimizing pressure on other bodily functions. The inner diameter of the upper ring 200 for the front 210 and back 220 surfaces of the device ring 200 extend further into the interior dimensions of the device walls 210a, 220b, by a range of 0.5 min to 6 min. The right 230c and left 230b sides of the upper ring 200 extend outwards from the walls 250c, 250b, anywhere from 0.5 mm to omin. The existence of the upper ring 200 extending outwards from the cup walls 270 is not unique per se, but this particular extension of the ring 200 outwards from the device wall 270 is substantial enough to assist in creating a seal when placed within the vaginal cavity, while not extending out in width to the point of creating intense pressure or rigidity due to excessive material volume dimensions. Further comprising, the upper ring 200, does not uniformly extend inside 210a, 220b, from the walls 270, nor outwards 230b, 230c, from the walls 270 as other devices, but this particular ring 200 design is useful in that it reduces or eliminates undue pressure, bruising, soreness, or discomfort due to a malleable and minimal material dimension that eliminates what is typically a stiff upper ring. It should be noted that the upper ring 200 at the front facing side 210 may reduce pressure in areas such as the urethra. FIG. 13, FIG. 14, while the back side 220, may reduce pressure on the colon due to being more flush with the cup walls 270. Alternatively, the upper ring 200 may uniformly extend inside the cup walls, or outside the cup walls 270.

Figure 3:
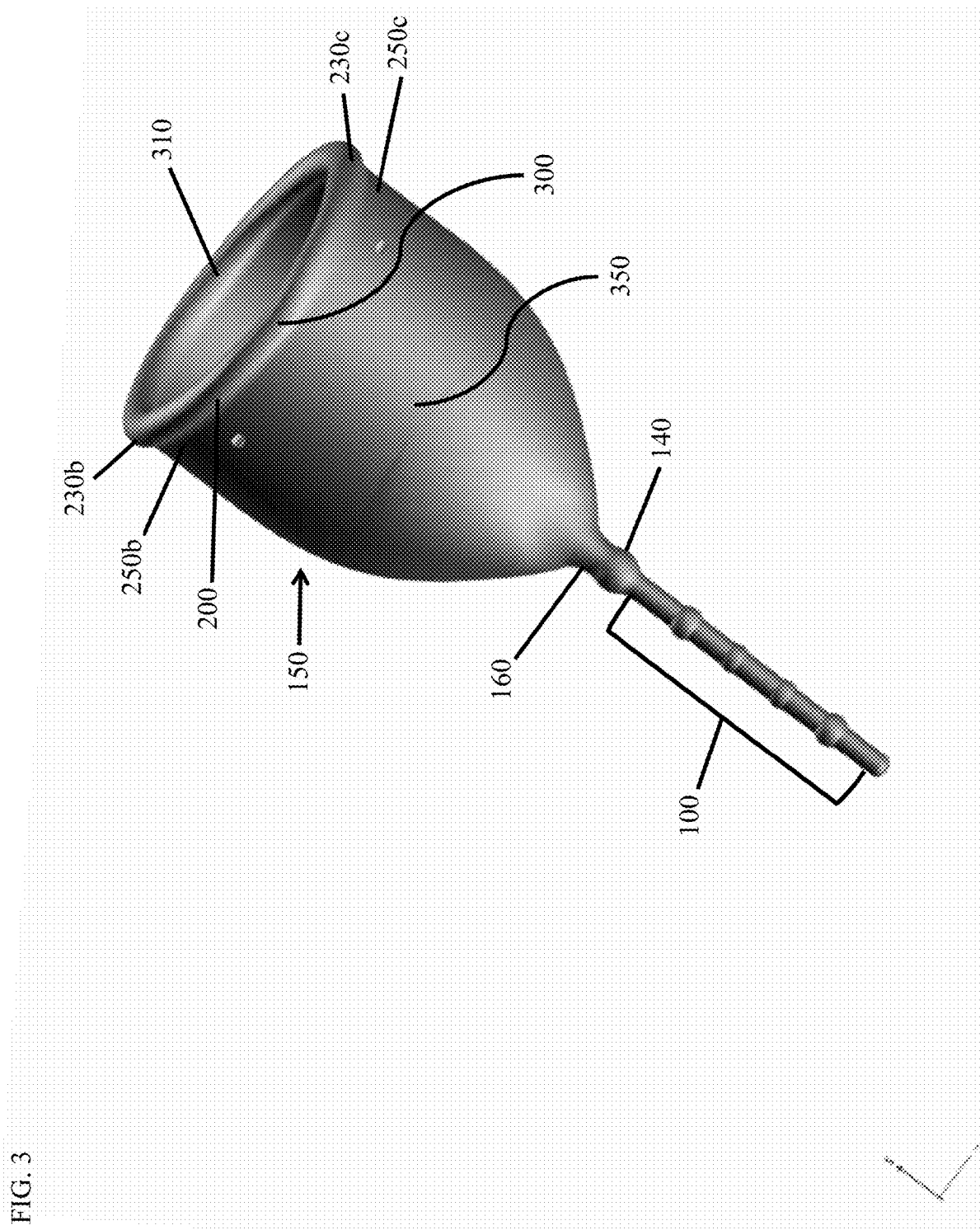
FIG. 3 is perspective view of a menstrual device from the front at an angle of the present invention.

In the exemplary perspective view of FIG. 3, the small removal bulb 140 at the base of the device 160 provides a place to hold securely and pull to remove the device 150. Further comprising, pulling anywhere along the elongated stem 100 or removal bulb 140 downwards, or from side to side can break the seal of the upper ring 200 and ease removal. Further, from this perspective view, the front side of the upper ring 300 is noticeably lower than the back side of the upper ring 310. This is due, in part, to a shorter front wall 350, which is unique in that during removal, the shorter front wall 350 assists in breaking the seal of the upper ring 200, thereby minimizing prolonged suction or discomfort. Further, the shorter front wall 350 provides greater comfort to the user during removal as it allows more flexibility as the now fully opened upper ring 200 is pulled out from the vaginal canal FIG. 14. It should be noted that from this perspective view the sides 230b, 230c of the upper ring 200 visibly protrude outward from the cup walls 250b, 250c.

Figure 4:
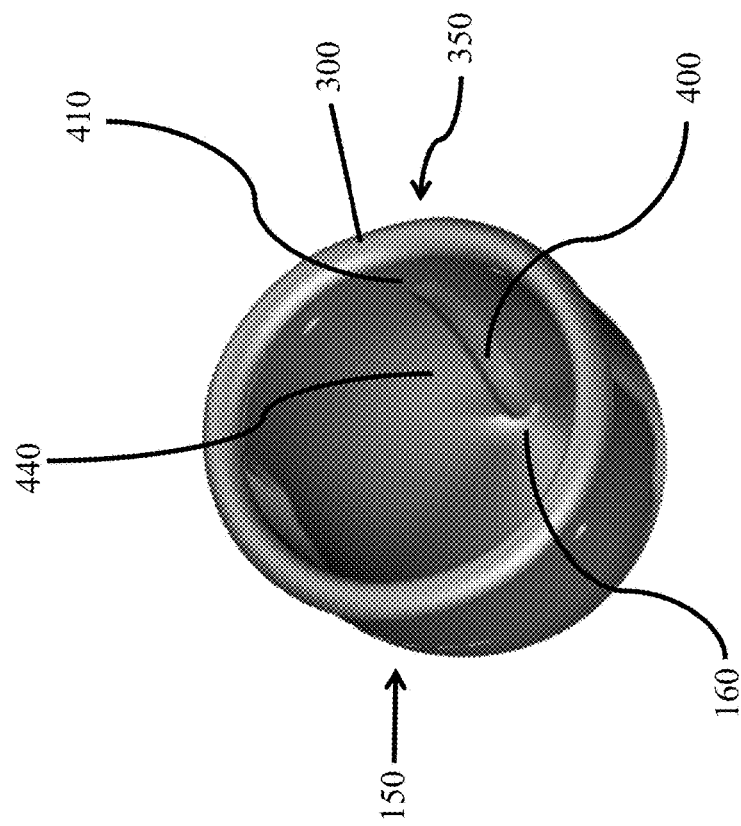
FIG. 4 is a perspective view into the internal walls of a menstrual device at an angle that shows the inside of the front and side walls, as well as the internal spine.

In the exemplary perspective view of FIG. 4, an internal spine 400 extends from the base of the device 160 up the inside wall 440 of the front side of the device 350. Alternatively, the internal spine 400 can, but does not need to, extend the full length of the device 410. This is in part due to the slight dip in the front of the upper ring 300, which assists in creating a crease, fold, or "hinge" when pressure is applied to the front wall 350, as demonstrated in FIG. 8. The internal spine 400 assists in the device 150 folding with pressure applied in one or more locations on the device front wall 350, as demonstrated in FIG. 7 through FIG. 12. Further comprising, the internal spine 400 assists in the device 150 fully opening, once placed inside the vaginal cavity FIG. 14, from the collapsed positioning, as demonstrated in FIG. 10 through FIG. 12.

Alternatively, the internal walls 440 of the device 150 remain substantially smooth, without the presence of an internal spine 400 or additional material protruding in width.

Figure 5:
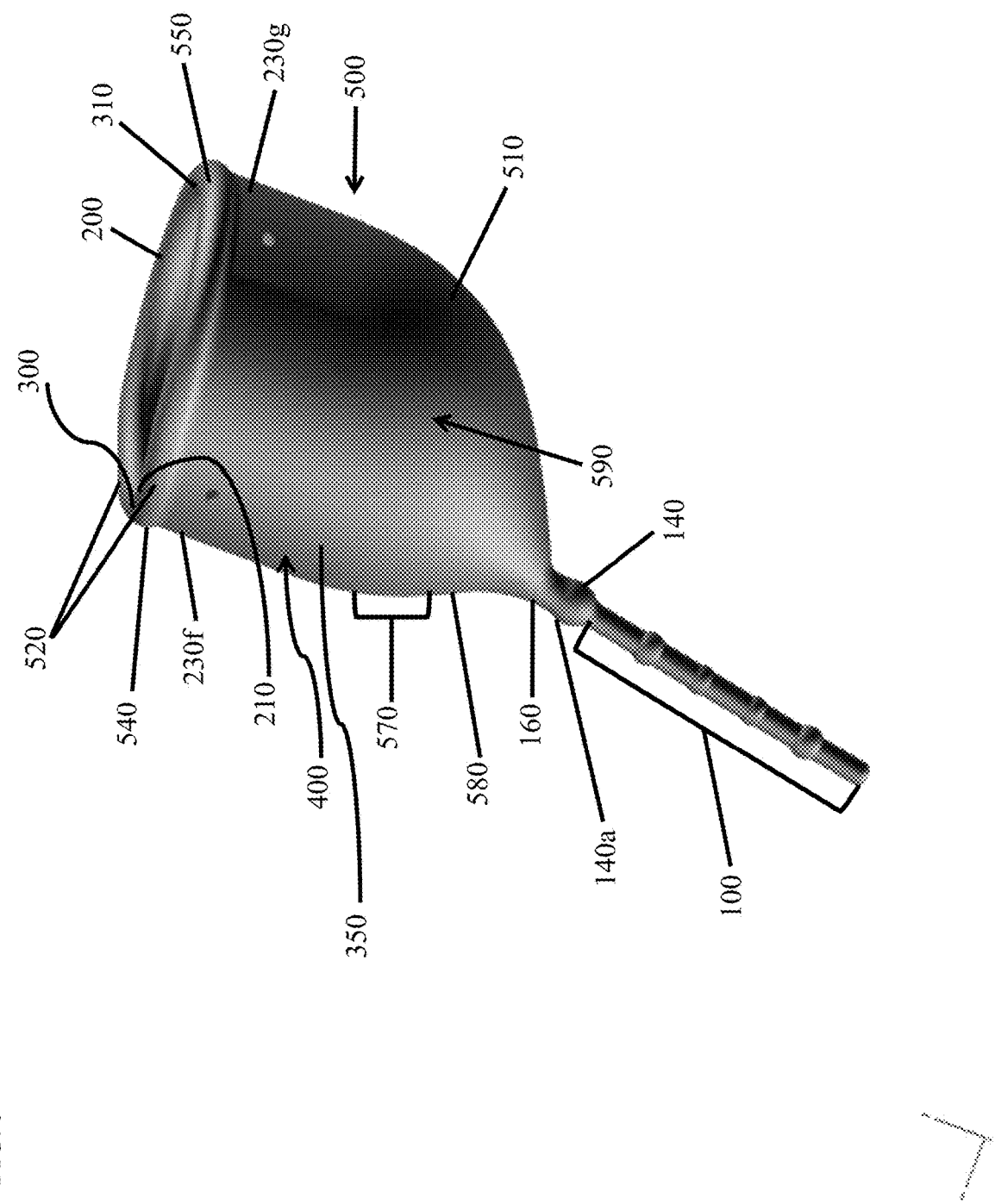
FIG. 5 is a perspective view of a menstrual device from the side.

In the exemplary perspective view of FIG. 5, the front outer edge of the upper ring 540, and back outer edge of the upper ring 550 are more flush with the cup walls 230f, 230g. The front 540 and back 550 upper ring extends between 0.05 mm and 5 mm outwards from the device walls 230f, 230g. The upper ring 200 has minimal volume of material in order to reduce the amount of pressure in the upper extremities of the device, which is useful because anatomically, the distances between the urethra, vaginal canal, and colon are closer together the further up you go from their openings, so less pressure at the top of the device, 540, 550, 200 is desired to reduce pressure on other organs and bodily functions. The upper ring 200 ranges from 2 mm to 7 mm in width. Further comprising, the specific aspects that are unique in the functioning of the upper ring 200 are that it applies less pressure to critical areas in the front 540 and back 550 of the device to the urethra and colon due to being more flush with the device walls 230f, 230g, thus distributing the pressure instead of intensifying it.

A second perspective view of FIG. 5, the internal spine 400 and asymmetrical, as demonstrated in FIG. 5, device shape 500 assist the device fully opening once inside the vaginal cavity. This particular design is useful because the upper ring 200, 300, asymmetrical device body 500, internal spine 400, individually, or in concert, helps to create an effective seal. The specific aspects unique in their functioning are that they can eliminate the need for increased skin contact to manually facilitate the device opening fully. Further comprising, this particular design is useful because it can eliminate the uncertainty or guesswork that even the most experienced cup users exhibit as to whether an effective pop open or seal was created.

A third perspective view of FIG. 5, the asymmetrical shape 500 results in the device opening fully with integrity, and not relying on a stiff upper ring 200 for holding its shape within a constricting space. Further comprising, having a device body 500 with increased integrity and strength due to the asymmetrical shape 500 also eliminates the need for a drastic pop-open, or opening of the of the device upper ring 200, which in this particular design is useful because it reduces the potential for pain, bruising, or soreness in users. Further comprising, it minimizes the intensity of the suction from the seal when removing the device.

Figure 8:
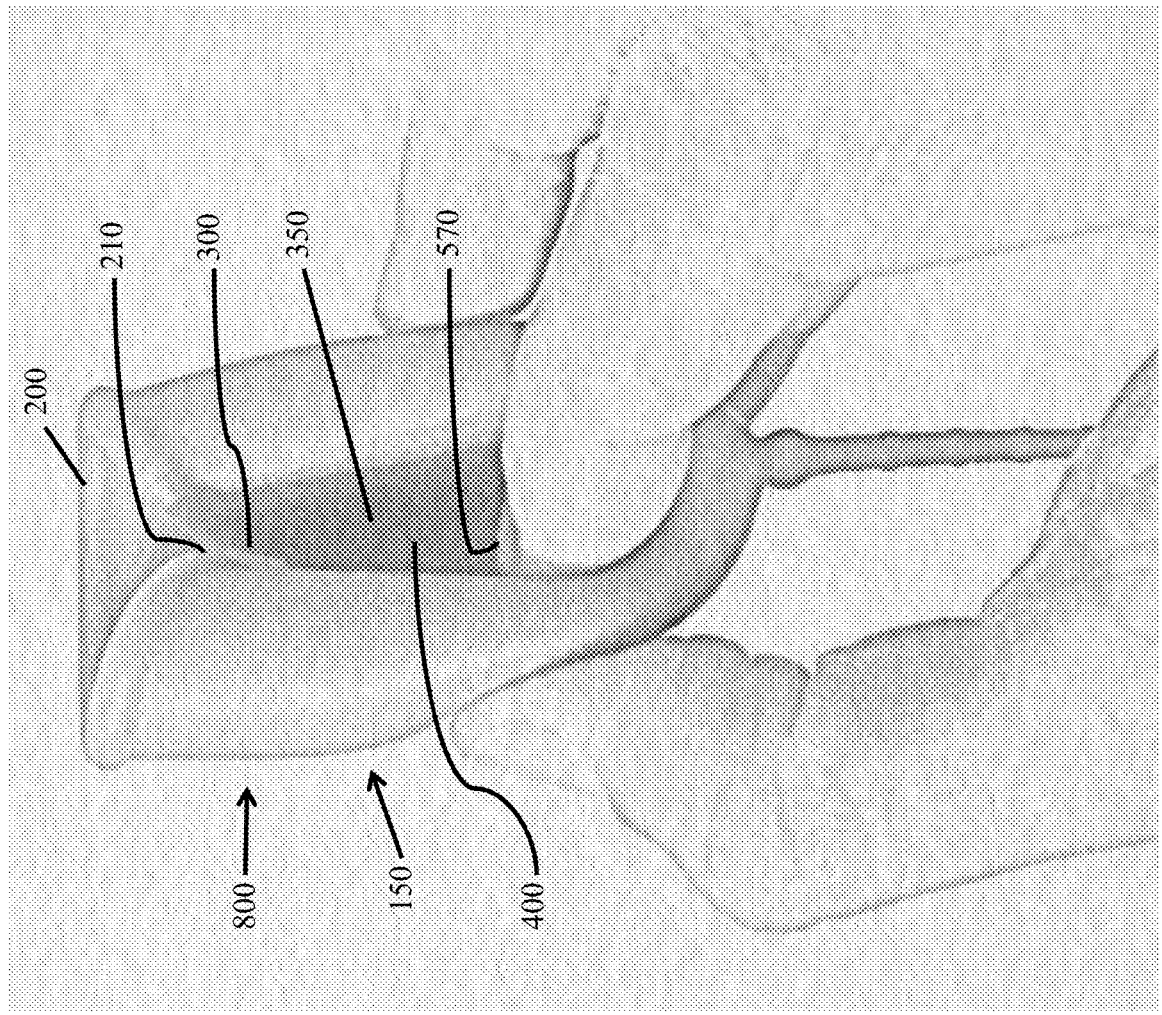
FIG. 8 is a perspective view of a pressure point near the base of a menstrual device being pressed to fold and collapse the device.
Figure 9:
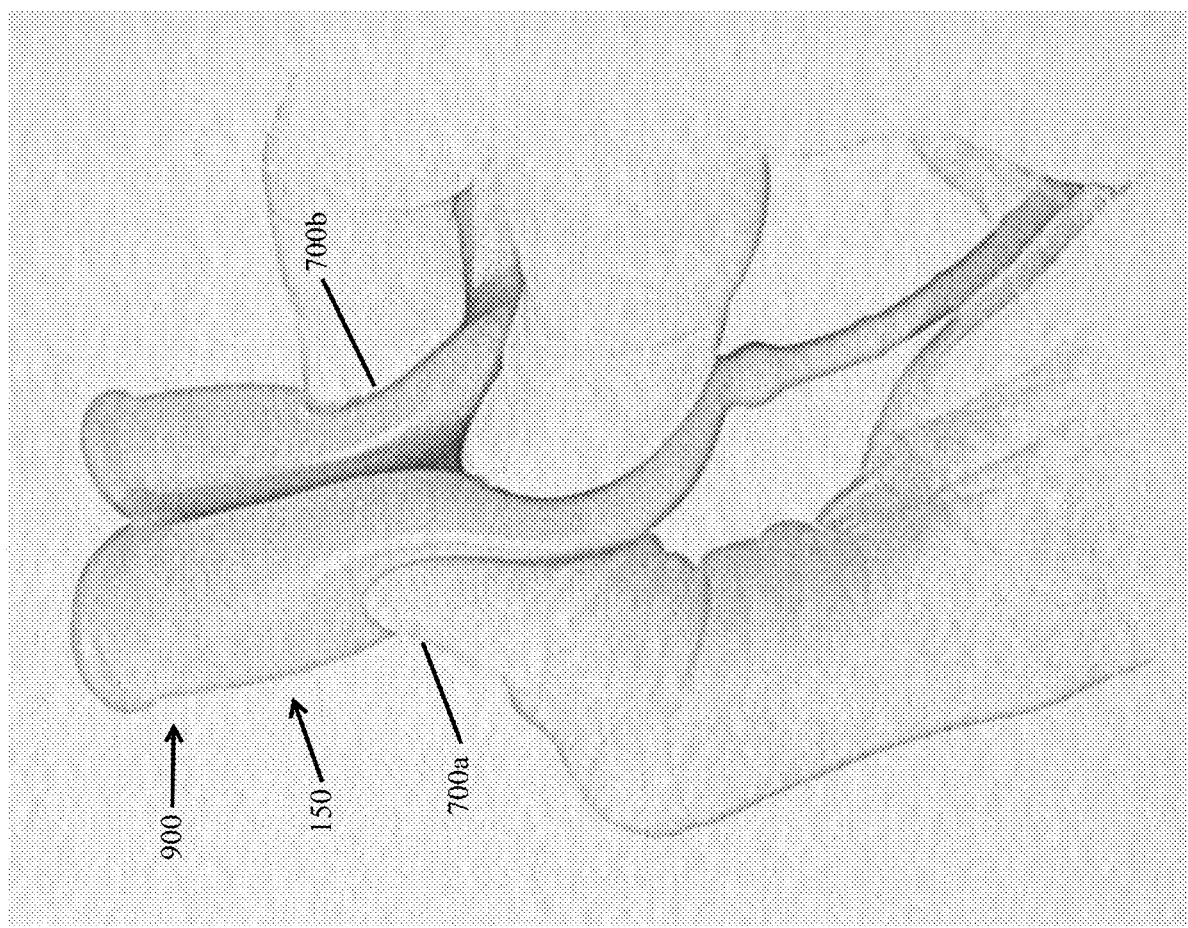
FIG. 9 is a perspective view of a menstrual device folding and side walls being pressed together.
Figure 10:
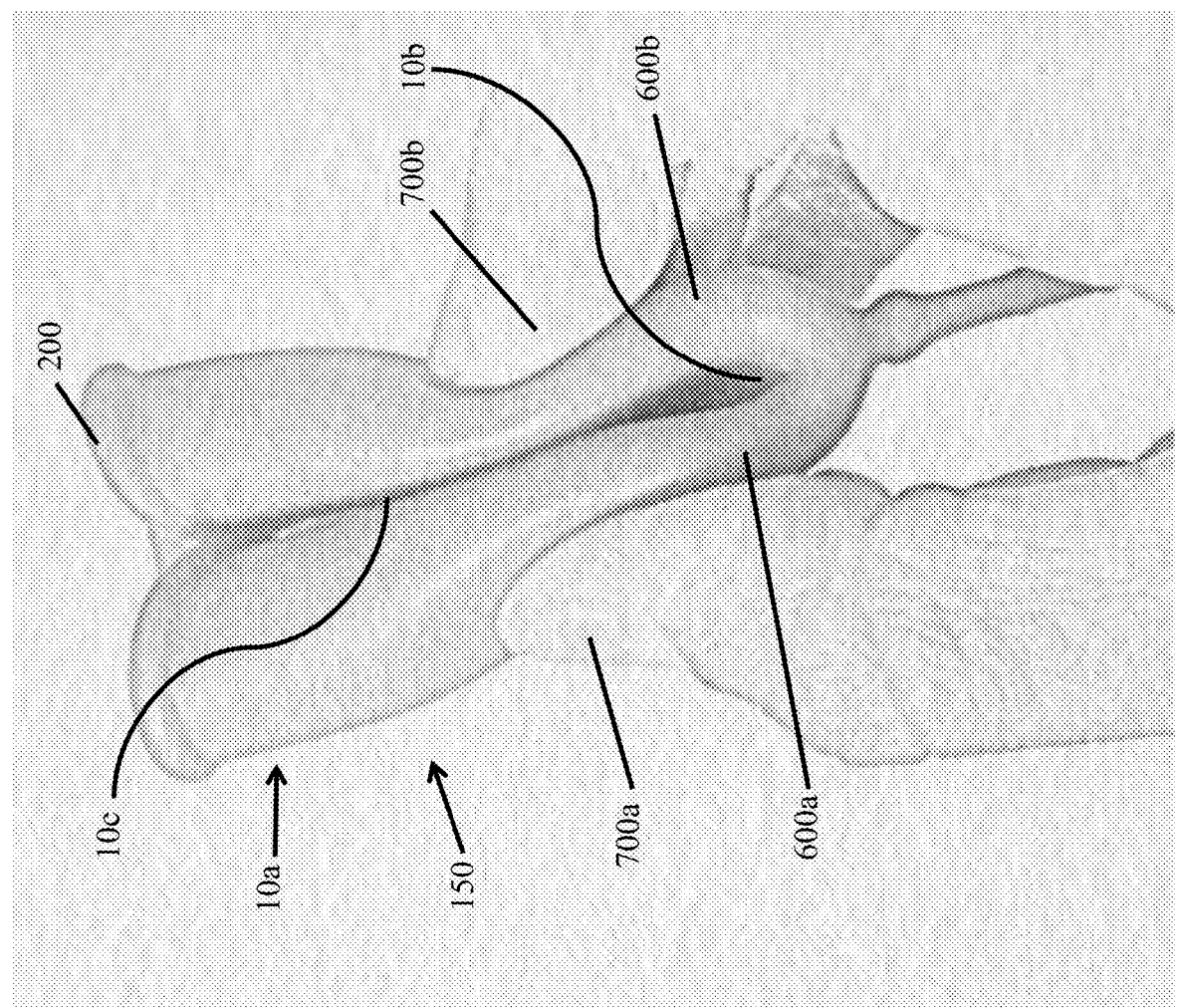
FIG. 10 is a perspective view of a menstrual device collapsed into a fold and held together.
Figure 11:
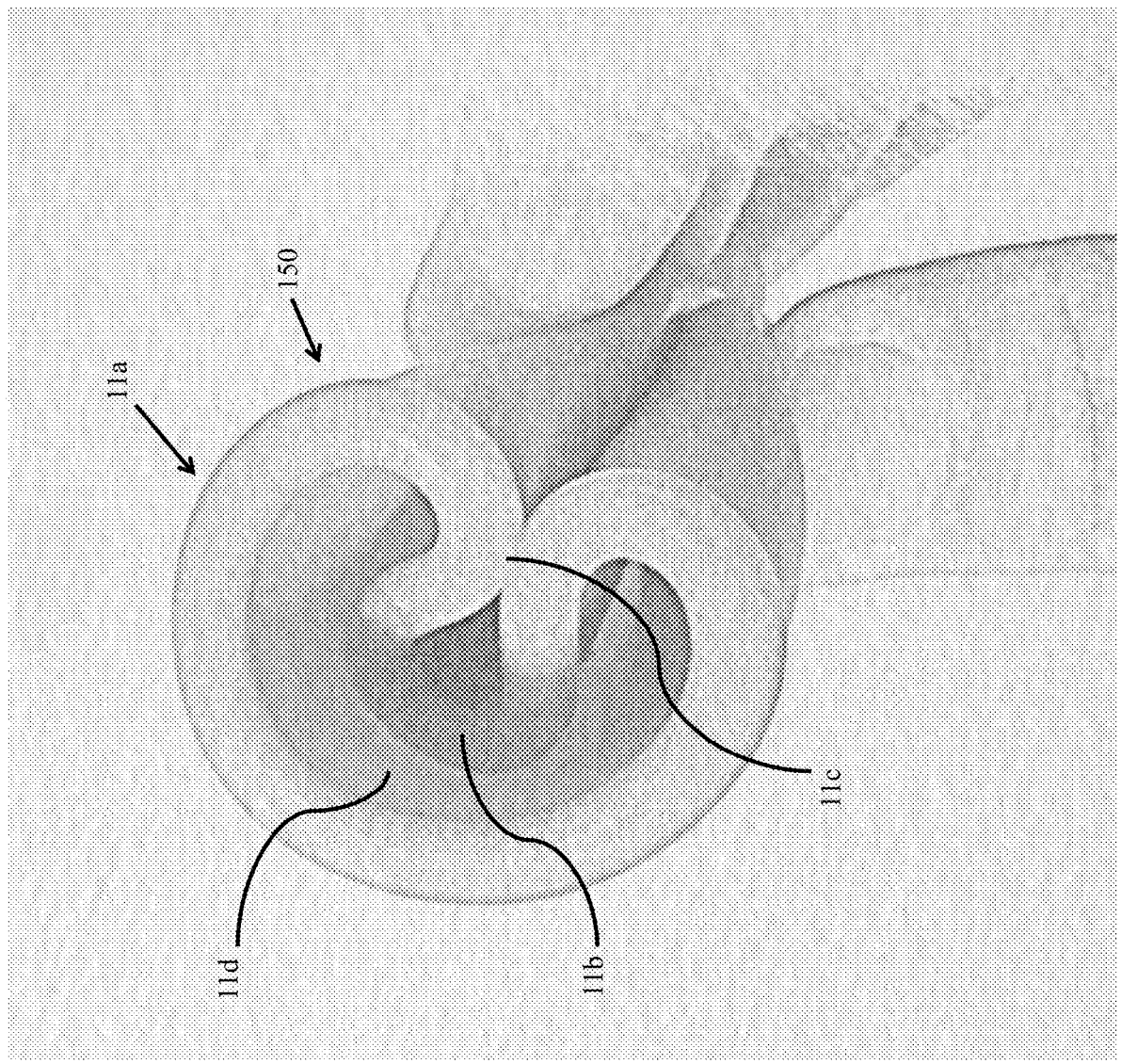
FIG. 11 is a perspective view from the top of a folded menstrual device being held in place.
Figure 12:
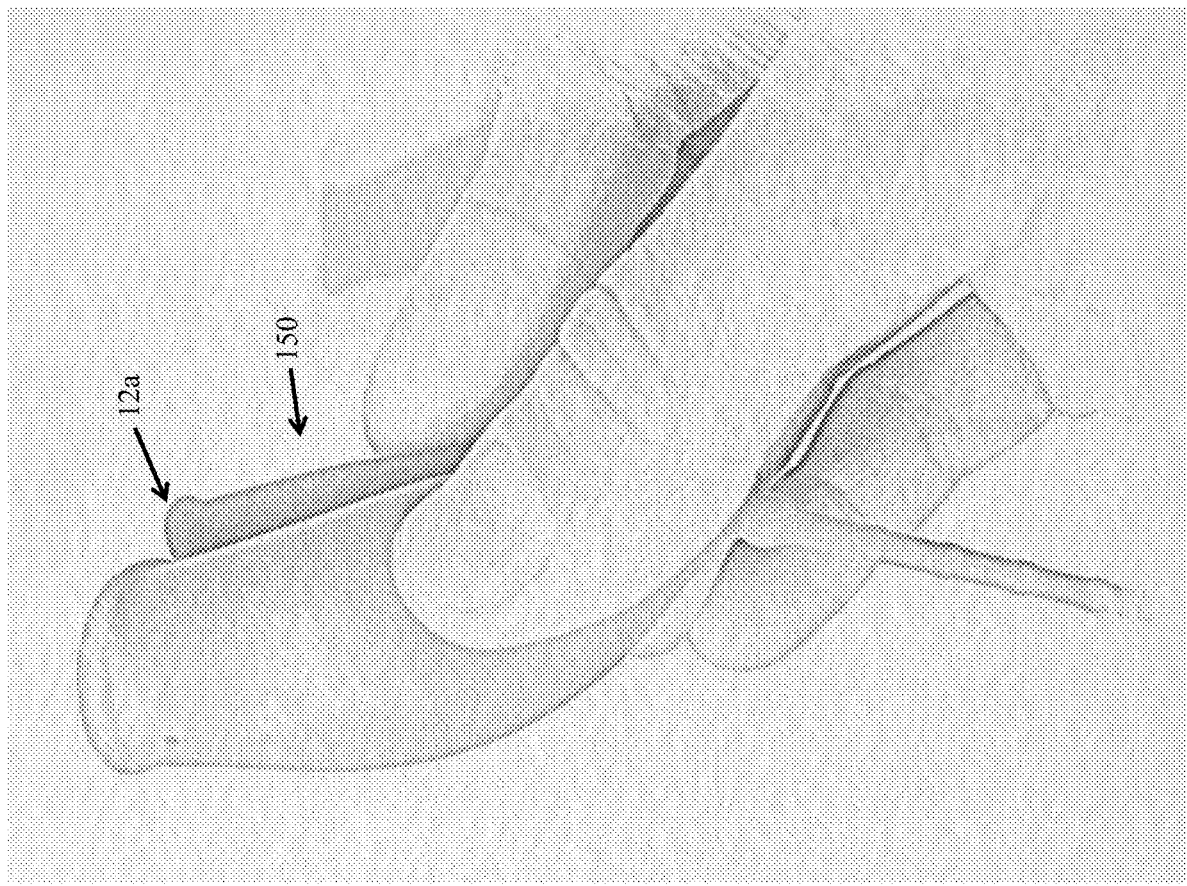
FIG. 12 is a side perspective view of a folded menstrual device ready for insertion into a vaginal canal.

A fourth perspective view of FIG. 5, a pressure point 570 within the lower third of the device front wall 350 allows for one-handed folding of the device and can eliminate the need for handling and touching upper regions of the device 500 to create a fold, as demonstrated in FIG. 7 through FIG. 12, that collapses the device walls and concentrates the device circumference so as to prepare for insertion into the vaginal canal, FIG. 10 through FIG. 12. Further comprising, the asymmetrical device 500 also curves 580 towards the base 160 from near the pressure point 570. This particular curvature 580 near the pressure point is useful because it helps the user to identify the front side of the cup 350 from near the base 160, the location of the pressure point 570, as well as conforms to contours within the vaginal wall FIG. 13 and FIG. 14. Further comprising, the curvature 580 minimizes potential for bruising or soreness of pressure placed against the pubic bone, but instead, due to complimentary contours, further assists holding the cup in place FIG. 14. It should be noted, that the curvature 580 also enables users to identify from just above the base 160 when placing the device where the front facing wall 350 is located due to the slender curve 580 as opposed to the more bulbous curve of the back side 510, which due to it's shape and placement within the vaginal cavity, enables significant collection of fluids.

A fifth perspective view of FIG. 5, the removal bulb 140 in this particular device is placed forward of the cup center line 590, and angled forward as if towards the user's toes when standing, not directly downwards and parallel to the cup center point 590. This unique placement is useful in that it better conforms to anatomy and compliments contours. Further comprising, the angle 160 enables effective stem 100 placement for function, providing logical placement for removal in that the stem 100 goes towards the vaginal opening, which increases comfort as well since the stem material isn't probing into the vaginal canal or into the labia. Similar to how a user using a tampon would need to insert it towards their lower back, and not directly up and towards their head, so too with a menstrual cup, hence the particular asymmetrical location for the removal stem 160, bulb 140, and angle of the stem 100. Further comprising, the unique stem placement not only creates a reference as to the cup placement and location, but also enables the cup to stay in place properly, as opposed to traditional cups that sometimes migrate or move out of position, thus causing discomfort or leaking. Further comprising, placement of the stem slightly forward not only simplifies the location for grabbing hold of the stem and base of the cup, but potentially benefits individuals with reduced mobility as well in that placement slightly forward means not having to reach back as far as traditional stems that are positioned and angled directly down.

A sixth perspective view of FIG. 5, the upper ring 520, forward of the cup center line 590, is sloping towards the front 300, creating an asymmetrical and sloping upper ring 200 resulting in a higher height in the back wall 310 of the device than the front wall 350. Further, the lower front wall 350 and ring 520 of the device results in less material and device circumference when folding the device 500 in preparation to insert, as is visible in FIG. 11, enabling greater ease and comfort for the user when placing the device. Further comprising, this particular design is useful because with the shorter front wall 350 and the asymmetrical upper ring 520, less pressure 570 is required to create the fold and collapse the device, thereby enabling the option of using the device with just one hand, as well as eliminating the need to touch additional areas of the device. Further comprising, the upper ring 540 material shifts further towards the inner wall 210, thereby is further usefid in that it creates an easier "hinge" or crease for the fold when pressure is applied 570 as there is less material that might otherwise bunch and create resistance at 540.

A seventh perspective view of FIG. 5, the unique shape 500 which allows for substantial volume of menstrual fluid collection, retains the integrity of the device shape, yet conforms to natural bodily contours 510, 580, 160. The overall shape of the device body 500 ensures wall integrity and comfort with its asymmetrical shape 500. This particular asymmetrical shape 500, is useful because the front facing wall 350 has the slight curvature 580 that connects to the base 160, while the back wall 510 is more bulbous, with curvature that conforms to the female anatomy. Further comprising, the angle of the upper ring 520 assists users who may have a lower cervix, thereby possibly, eliminating: potential disruption of proper placement within the vaginal canal; interference with the device fully opening; or possible bruising of the cervix. Further comprising, the removal bulb 140 has the option to be asymmetrical with less material protruding on the front facing side 140a in order to be more flush with the vaginal wall, thereby potentially further reducing any pressure.

Figure 6:
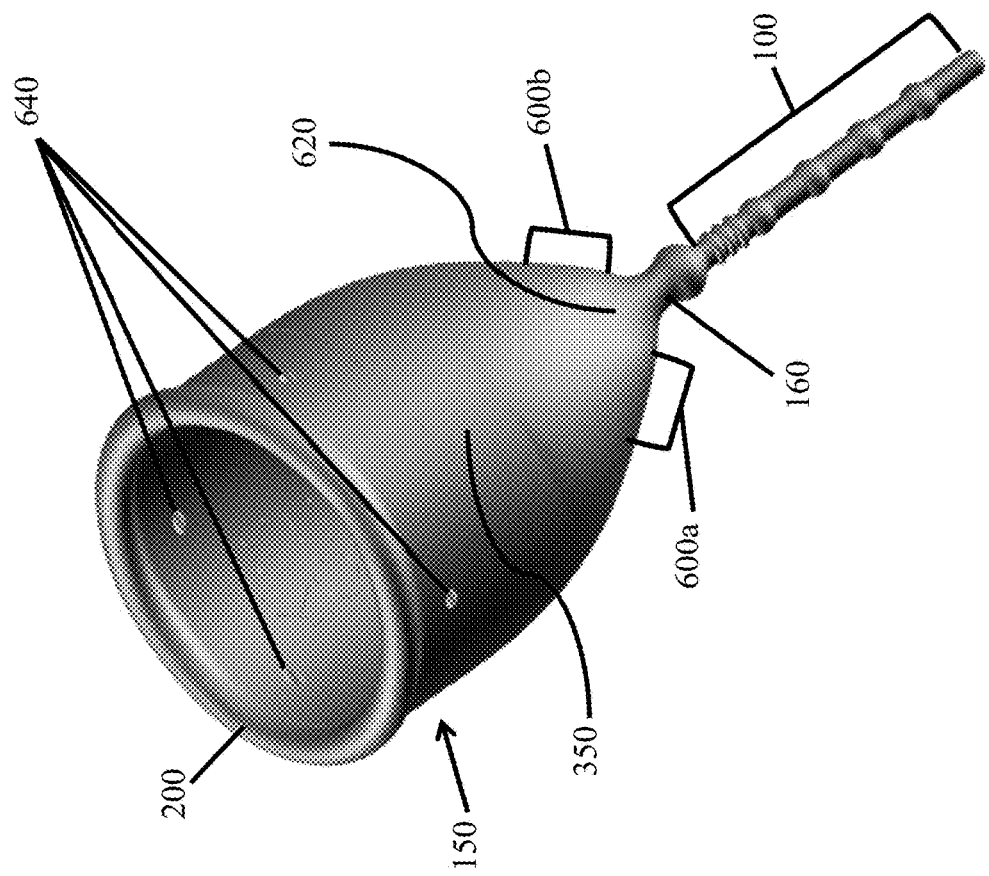
FIG. 6 is a perspective view of a menstrual device from the front at an upper angle.

In the exemplary perspective view of FIG. 6, the two points 600a, 600b above the device base 160, equidistant from the front of the device 350, can be pressed or pinched together in order to assist the device fully popping open, if needed, to create the seal of the upper ring 200. The existence of these unique pressure points can be useful if the device does not fully open upon initial placement FIG. 14, because, for example, the user has a tighter vaginal cavity. In which case, the pressure points 600a, 600b located in the lower quarter of the device 150, can have pressure applied from opposite sides to facilitate opening of the device. This specific aspect is unique in the functioning because it encourages the desired opening of the device with minimal guesswork or contact further up the device and into the vaginal canal to check that the seal 200 is fully intact. Further comprising, the user can determine if the device is fully open from base 620, as opposed to having to reach further into the vaginal canal to manually determine this, due to the fold, as demonstrated in FIG. 10, that the user can feel at the front base 620 of the cup 150. Further comprising, the removal stem 160 has the option of being asymmetrical in shape to further enable flexibility of movement.

A second perspective view of FIG. 6, if assistance is needed to comfortably and effectively break the seal 200 for removal, direct pressure can be placed gently near the base 620 of the device, which will effectively break the seal of the upper ring 200. Further comprising, a user may gently guide the cup 150 towards the vaginal opening by pulling down or side to side on the stem 100, then when the cup 150 is almost completely removed, holding securely at the now visible and accessible base 160 with the option of pressing gently on the pressure point 620 to break the seal. This approach is possible in part due to the elongated stem 100, as well as the pressure point at the base of the cup 620 functioning in concert with the upper ring 200 to reduce the pressure and circumference of the upper ring 200, thereby better controlling and minimizing potential spillage while emptying menstrual material from the cup.

A third perspective view in FIG. 6 illustrates where the one or more pressure or cup seal holes 640 to balance bodily functions while placed inside the vaginal canal are visible near the upper ring 200 of the device. It should be noted that they are not a unique design feature.

Figure 7:
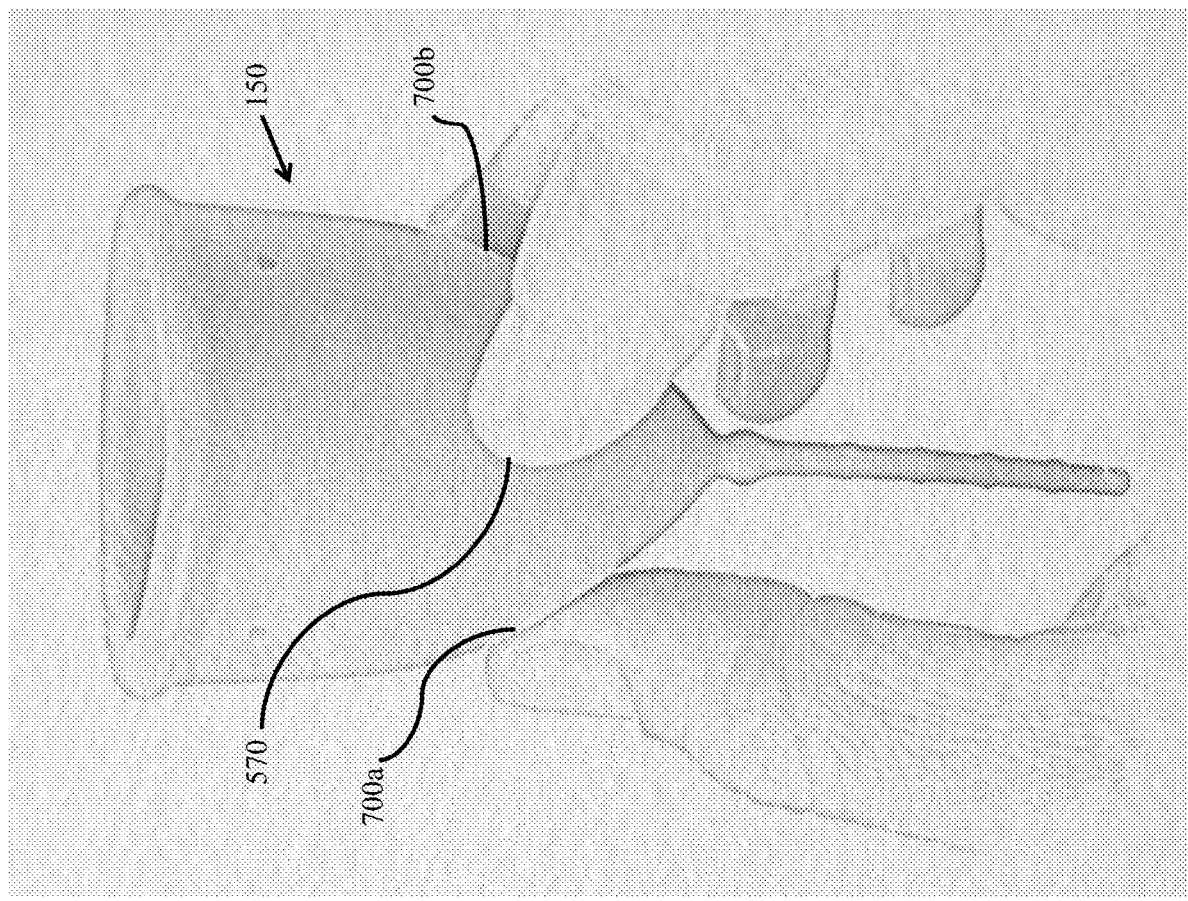
FIG. 7 is a perspective view of holding a menstrual device.

In the exemplary perspective view of FIG. 7, the device 150 is held in one hand with two fingers, such as the thumb and middle finger, on opposite sides of the lower third of the cup body 700a, 700b, and finger, such as the index finger, touching the pressure point 570. Further comprising, the device 150 has the option of including additional grips or material near the base that extends from the device walls in order to provide additional traction while contacting the cup for collapsing, or for removal.

In the exemplary perspective view of FIG. 8, the device 150 is shown with pressure applied 800 to the front wall 350 at the pressure point 570, which coincides with the internal spine 400. The upper ring 200 is shown collapsing at the front-facing, lowest point 300, further assisted by the upper ring material 210 that extends further into the cup walls, thereby creating a hinge.

In the exemplary perspective view of FIG. 9, the device 150 is shown collapsed 900. Side walls 700a, 700b continue to be pressed together with the two or more fingers.

In the exemplary perspective view of FIG. 10, the device 150 is shown fully collapsed 10a. The fold 10c on the front facing side of the cup extends from the upper ring 200 down to the base 1101), thereby enabling a user to feel and identify from the base of the cup whether it is fully open or still partially collapsed while it is placed inside the vaginal canal FIG. 14. Further comprising, in the event that the device 150 does not fully open, for example in a user who has a narrower vaginal canal when first inserting the cup, and the pressure collapsing the cup 700a, 700b is removed, the user may apply pressure on the lower portion of the cup base 600a, 600b, to encourage full opening of the device.

In the exemplary perspective view of FIG. 11, the device 150 is shown from above in a collapsed configuration 11a. Further comprising, the asymmetrical shape and shorter front wall when collapsed 11b does not bunch material from the entire upper ring onto each other 11c, but rather is offset 11d in most areas, thus resulting in creating a smaller overall cup dimension when collapsed.

In the exemplary perspective view of FIG. 1, the device 150 is shown fully collapsed 12a and ready for insertion into the vaginal canal.

These, along with other details of this unique design, will become more apparent in the following claims and drawings. It is understood that there may be some changes to the exact structure described and shown, but they do not negate the overall spirit of the invention. Further, features described in the preceding description may be used in combinations other than the combinations explicitly described.

Whilst aiming to draw attention to features of the invention believed to be of particular importance, it should be understood that the Applicant claims protection in respect of any patentable feature or combination of features hereinbefore referred to and/or shown in the drawings whether or not particular emphasis has been placed thereon.

The term "comprising" as used in the claims does not exclude other elements or steps. The term "a" or "an" as used in the claims does not exclude a plurality. A unit or other means may fulfill the functions of several units or means recited in the claims.

What is claimed is:

1. A device for collecting and holding menstrual fluids within a user's body, the device comprising:
    an asymmetrical cup that tapers downward to a base, wherein the asymmetrical cup is open at an upper edge to collect the menstrual fluid, and closed at a lower edge to contain the fluid in the cup, the cup further comprising:
        an inner wall configured to contact the collected menstrual fluid;
        an outer wall configured to contact and form a seal against a user's vaginal wall; and
        at least one pressure point on the asymmetrical cup;
    an upper ring that extends outwards from the upper edge of the cup, wherein the upper ring is substantially flush with the outer wall on an upper, front facing side of the cup, the upper ring extending inside the cup walls, thereby minimizing pressure on a urethra of the user.

2. A device, as described in claim 1, further comprising a removal stem singly molded with the base of the device in uniform material, extending downward from the base of the cup, the stem configured to be adapted to extend an adjustable length from the base of the cup.

3. A device, as described in claim 1, wherein the at least one pressure point enables folding, closure, or collapsing of the device into a smaller compacted area while maintaining structural integrity of the device to fully open once positioned and released.

4. A device, as described in claim 1, wherein the at least one pressure point is positioned near the base of the asymmetrical cup.

5. A device, as described in claim 1, further comprising an internal spine, configured to assist in returning the device to the fully open position after the device is placed inside a vaginal cavity of the user.

6. A device, as described in claim 1, wherein the seal against the user's vaginal wall can be broken during removal due in part to at least one of:
    compression of a pressure point near the base;
    asymmetrical cup design with a shorter wall; and
    angled upper ring.

7. A device, as described in claim 2, wherein the placement of the removal stem is forward of the cup geometric center and continues outwards and down from a front facing wall of the cup, thereby configured to be held by the user near a labia of the user during removal.

8. A device, as described in claim 2, wherein the removal stem is of a variable in width and further comprises one or more bulbs or grips for removal, the one or more bulbs further providing a reference if the user wishes to alter a length of the removal stem.

9. A device, as described in claim 1, wherein the asymmetrical dimensions of the cup provides rigidity and structural integrity.

10. A device, as described in claim 1, wherein the front facing side of the cup and upper ring has a shorter height than a taller back side of the device which allows the device to have a smaller amount of material circumference, due to the asymmetrical design, when folded and compacted for insertion.

11. A device, as described in claim , wherein a front facing wall of the base:
conforms to the user's body when placed in a vaginal canal above the pubic bone,
further assists the cup staying in place,
indicates an orientation of the front facing wall while inside the vaginal canal from the base, and
further indicates a location of the at least one pressure point.

12. A device for collecting and holding menstrual fluids within a user's body, the device comprising:
an asymmetrical cup that tapers downward to a base, wherein the asymmetrical cup is open at an upper edge to collect the menstrual fluid, and closed at a lower edge to contain the fluid in the cup, the cup further comprising:
an inner wall configured to contact the collected menstrual fluid;
an outer wall configured to contact and form a seal against a user's vaginal wall; and
at least one pressure point on the asymmetrical cup; and
an upper ring that extends outwards from the upper edge of the cup, wherein the upper ring is substantially flush with the outer wall on an upper, rear facing side of the cup, the upper ring extending inside the cup walls, thereby minimizing pressure on a colon of the user.

13. A device, as described in claim 12, further comprising a removal stem singly molded with the base of the device in uniform material, extending downward from the base of the cup, the stem configured to be adapted to extend an adjustable length from the base of the cup.

14. A device, as described in claim 12, further comprising a removal stem with one or more bulbs for removal, the removal stem molded with the base of the device in uniform material, extending downward from the base of the cup.

15. A device for collecting and holding menstrual fluids within a user's body, the device comprising:
an asymmetrical cup that tapers downward to a base, wherein the asymmetrical cup is open at an upper edge to collect the menstrual fluid, and closed at a lower edge to contain the fluid in the cup, the cup further comprising:
an inner wall configured to contact the collected menstrual fluid;
an outer wall configured to contact and form a seal against a user's vaginal wall; and
at least one pressure point on the asymmetrical cup; and
an upper ring that extends outwards from the upper edge of the cup, wherein the upper ring both extends outwards from the outer wall of the cup and extends inwards from the inner wall of the cup, with a dip in a front of the upper ring that assists in creating a crease, fold, or hinge.

16. A device, as described in claim 15, further comprising a removal stem singly molded with the base of the device in uniform material, extending downward from the base of the cup, the stem configured to be adapted to extend an adjustable length from the base of the cup.

17. A device, as described in claim 15, further comprising a removal stem with one or more bulbs for removal, the removal stem molded with the base of the device in uniform material, extending downward from the, base of the cup.

18. A device for collecting and holding menstrual fluids within a user's body, the device comprising:
an asymmetrical cup that tapers downward to a base, wherein the asymmetrical cup is open at an upper edge to collect the menstrual fluid, and closed at a lower edge to contain the fluid in the cup, the cup further comprising:
an inner wall configured to contact the collected menstrual fluid;
an outer wall configured to contact and form a seal against a user's vaginal wall; and
at least one pressure point on the asymmetrical cup; and
an upper ring that extends outwards from the upper edge of the cup, wherein the upper ring is asymmetrical and can have a variable diameter size.

19. A device, as described in claim 18, further comprising a removal stem singly molded with the base of the device in uniform material, extending downward from the base of the cup, the stem configured to be adapted to extend an adjustable length from the base of the cup.

20. A device, as described in claim 18, further comprising a removal stem with one or more bulbs for removal, the removal stem molded with the base of the device in uniform material, extending downward from the base of the cup.

* * * * *